United States Patent [19]

Johnson et al.

[11] 4,017,424

[45] Apr. 12, 1977

[54] HYDROCARBON STEAM REFORMING AND METHANATION CATALYSTS

[75] Inventors: Marvin M. Johnson; Gerhard P. Nowack, both of Bartlesville, Okla.

[73] Assignee: Phillips Petroleum Company, Bartlesville, Okla.

[22] Filed: Oct. 1, 1975

[21] Appl. No.: 618,722

[52] U.S. Cl. .............................. 252/437; 252/470; 252/473

[51] Int. Cl.$^2$ .................... B01J 27/14; B01J 23/64

[58] Field of Search .................. 252/437, 470, 473

[56] References Cited

UNITED STATES PATENTS

| | | | |
|---|---|---|---|
| 2,442,319 | 5/1948 | Britton et al. | 252/437 X |
| 3,149,081 | 9/1964 | Bowman et al. | 252/437 |
| 3,298,966 | 1/1967 | Bagnetto | 252/437 X |
| 3,420,887 | 1/1969 | Noddings et al. | 252/437 X |
| 3,501,549 | 3/1970 | Noddings et al. | 260/680 |
| 3,595,808 | 7/1971 | Bertsch et al. | 252/437 |
| 3,600,145 | 8/1971 | Johnson et al. | 252/437 X |
| 3,625,647 | 12/1971 | Stowe | 252/437 X |
| 3,630,967 | 12/1971 | Nicklin et al. | 252/470 X |
| 3,708,550 | 1/1973 | Benther et al. | 252/437 X |
| 3,847,836 | 11/1974 | Nicklin et al. | 252/470 X |

*Primary Examiner*—Winston A. Douglas
*Assistant Examiner*—John F. Niebling

[57] ABSTRACT

A catalyst consisting essentially of nickel, a promoter selected from the group consisting of barium and uranium and a calcium phosphate support having a Ca:P atomic ratio in the range of 1.4:1 to 2.3:1, is formed by impregnating a calcium phosphate gel with suitable compounds of nickel and either barium or uranium. The resulting catalysts are useful in steam reforming processes for producing methane.

11 Claims, No Drawings

HYDROCARBON STEAM REFORMING AND METHANATION CATALYSTS

This invention relates to novel catalytic materials and to catalytic processes. In one aspect this invention relates to novel catalytic materials. In another aspect this invention relates to the preparation of novel catalytic materials. In yet another aspect this invention relates to catalytic conversion processes.

Utility companies which distribute gas for household or other use have an increasingly acute need for an economical means of supplying gas during peak-load periods. During cold weather, for example, demand may be double or triple the volume used on a mild day. In many instances, the peak-load demand is met by adding propane-air mixtures to the gas. Because the quantity of propane-air that can be blended is limited, there is a need for an economical process that can be used to supply peak-load demand.

The reforming of paraffinic hydrocarbons with steam has become a well established process. The process produces mixtures of methane, hydrogen, oxides of carbon and small quantities of higher hydrocarbons such as ethane. Various catalysts are known or such reforming processes; however, relatively few such catalysts have been able to maintain their activity for a sufficiently long period to make their use practical.

Methanation by steam reforming carbon monoxide is also a well known process. The process produces a mixture of methane, carbon monoxide, carbon dioxide and hydrogen. Various catalysts are known for such methanation processes, however, many such catalysts produce methane containing an undesirable amount of carbon monoxide which can be difficult to separate. Further, carbon monoxide in admixture with methane is highly undesirable because of the high toxicity of the carbon monoxide in the event leaks occur in supply lines or in storage containers.

It is an object of this invention to provide a new and improved catalyst useful for steam reforming.

Another object is to provide an improved process for making a catalyst.

Yet another object is to provide a process for steam reforming hydrocarbon materials to a methane-containing gas.

A further object is to provide a process for methanation by steam reforming carbon monoxide.

Other objects, aspects and advantages of this invention will be readily apparent to those skilled in the art from the reading of the following disclosure and appended claims.

In accordance with the present invention there is provided a catalyst composition consisting essentially of nickel, a promoter metal selected from the group consisting of barium and uranium, combined oxygen and a calcium phosphate support having a Ca:P atomic ratio in the range of 1.4:1 to 2:3:1.

The catalyst compositions of this invention contain calcium, phosphorus, nickel and barium or uranium in the following amounts, expressed in terms of weight percent based upon the weight of the total catalyst:

|  | Broad | Preferred |
|---|---|---|
| Calcium | 5–35 | 10–25 |
| Phosphorus | 2–20 | 5–15 |
| Nickel | 10–50 | 20–40 |
| Barium | 1–20 | 2.5–18 |
| Uranium | 2–40 | 10–30 |

The difference between the sum of the percentages of the above-named elements and 100 percent is made up by the oxygen content of the catalyst in amounts sufficient to satisfy the valences of each of the elements in the catalyst.

In a presently preferred embodiment the support material has a Ca:P atomic ratio in the range of 1.5:1 to 1.8:1.

In a more preferred embodiment the support material has a Ca:P atomic ratio of 1.67 which corresponds to calcium hydroxyapatite, $Ca_5(OH)(PO_4)_3$.

The catalyst compositions of this invention are prepared by first preparing the calcium phosphate support. An aqueous solution of a soluble calcium compound is admixed with a soluble phosphate compound to form a calcium phosphate gel having a Ca:P atomic ratio in the range of 1.4:1 to 2.3:1.

Suitable calcium compounds include calcium acetate, calcium formate, calcium isobutyrate, calcium nitrate, and the like. Preferably, the calcium salt is one in which the anion portion is decomposed at calcination temperatures to a gas, leaving no undesirable residue. Suitable phosphate compounds include ammonium and Group Ia phosphates such as monohydrogen ammonium orthophosphate, sodium orthophosphate, monohydrogen sodium orthophosphate, monohydrogen sodium orthophosphate, dihydrogen sodium orthophosphate, trisodium phosphate, potassium orthophosphate, monohydrogen potassium orthophosphate, dihydrogen potassium orthophosphate, potassium pyrophosphate and the like.

In a presently preferred embodiment, all the phosphorus is combined with the calcium, none of the phosphorus being available for combination with the nickel or the promoter metals.

In one embodiment of this invention, the thus-prepared calcium phosphate gel is first combined with at least one of barium or uranium. The gel is filtered and washed, then reslurried in distilled water. Approximately one-half the desired amount of promoter metal in aqueous solution of a soluble promoter compound is added to the slurried gel. The mixture is allowed to stand for a period of time sufficient to ensure substantial uptake of the promoter in the wet gel. In general, this mixture should stand, with occasional stirring, for a period ranging from about 4 hours to about 4 days. This period may be shorter or longer, depending upon the promoter compound employed and the dilutions of the support gel and the promoter solution. To this mixture is added, with stirring, an aqueous solution containing a mixture of the remaining portion of the promoter compound and a soluble nickel compound, together with an alkaline solution of, for example, ammonium hydroxide, an alkali metal hydroxide or an alkali metal carbonate. The alkaline solution is added at a rate such that the pH of the mixture is at least 7, preferably in the range of 7 to 9. The resulting mixture is then filtered, washed, refiltered and dried in air at about 105° C.

In another embodiment of this invention, the nickel is first added to the calcium phosphate gel by adding an aqueous solution of a soluble nickel compound to the slurry of the calcium phosphate gel, with stirring, together with an alkaline solution of, for example, ammonium hydroxide, an alkali metal hydroxide or an alkali metal carbonate to maintain a pH of at least 7, preferably 7–9, in the resulting mixture. The nickel/calcium phosphate gel is then filtered, washed, refiltered and dried in air at about 105° C. The dried material is then impregnated with an aqueous solution of the promoter compound and re-dried at about 105° C.

The dry catalyst material can then be crushed, or otherwise reduced to granules or small lumps and be used directly; or it can, preferably, be pulverized, such as to a particle size capable of passing a 20–40 mesh screen, and the powdered product treated with a lubricant and pressed into the form of a pill or tablet or granule of size suitable for use as a catalyst. After forming, the catalyst material is calcined in the presence of an oxygen-containing gas or air at a suitable calcination temperature in the range of about 300°–650° C for a period of 30 minutes to 10 hours, or more. Prior to use, the calcined material is reduced with hydrogen at a temperature in the range of 300°–650° C for a period of 30 minutes to 10 hours, or longer, if necessary. Alternatively, the dried catalyst material can be reduced, as above, without prior calcination.

Suitable nickel compounds include nickel acetate, nickel nitrate and nickel sulfate. Suitable barium compounds include barium acetate, barium benzoate, barium butyrate, barium formate, barium nitrate, barium nitrite, barium propionate, barium salicylate and the like. Suitable uranium compounds include uranyl acetate, uranyl formate, uranyl nitrate and the like.

It is also within the scope of this invention to employ soluble halide compounds such as the nickel halides, barium halides and uranyl halides, such as the chlorides, bromides and iodides. It is further within the scope of this invention to employ calcium halide salts in preparing the support gel. However, due to the difficulty in removing the halide anions from the catalyst material during purification and calcining operations, the use of such halides is preferably avoided.

The catalysts of this invention are suitable for use in hydrocarbon conversion processes. In one embodiment of this invention there is provided a methanation process for the conversion of carbon monoxide by steam reforming to a gas containing methane and carbon dioxide, which comprises contacting a mixture of carbon monoxide and steam at an elevated temperature with the catalyst of this invention. The conversion is conducted at a temperature in the approximate range of 300°–1000° F (148°–538° C), at a pressure in the approximate range of 0–2000 psig (0 to 13.7 MPa) at a gaseous hourly space velocity (GHSV) for carbon monoxide in the approximate range of 100 to 10,000 and a carbon monoxide to steam mole ratio in the approximate range of 2:1 to 1:5.

It is presently preferred that the methanation process be conducted at a temperature in the approximate range of 400°–800° F (204°–427° C) at a pressure in the approximate range of 100 to 1,000 psig (0.689 to 6,89 MPa) and a carbon monoxide to steam mole ratio in the approximate range of 1:1 to 1:3.

It is presently preferred that the nickel on calcium phosphate catalyst used for methanation by reaction of CO and steam be promoted with uranium.

In another embodiment of this invention there is provided a process for steam reforming a hydrocarbon feedstock which comprises contacting a hyrocarbon feedstock having from 2 to 15 carbon atoms per molecule with steam and the catalyst of this invention at an elevated temperature. The reforming is conducted at a temperature in the approximate range of 650°–1200° F (343°–649° C) at a pressure in the approximate range of 0 to 2000 psig (0 to 13.7 MPa) at a liquid hourly space velocity (LHSV) for the feedstock in the approximate range of 0.1 to 10 and a steam to hydrocarbon weight ratio in the approximate range of 1:1 to 10:1.

It is presently preferred that the reforming process be conducted at a temperature in the approximate range of 700°–1000° F (371°–538° C), at a pressure in the approximate range of 100 to 1,000 psig (0.689 to 6.89 MPa) at an LHSV for feedstock in the approximate range of 1 to 5 and a steam to feedstock weight ratio in the approximate range of 1:1 to 5:1.

In a presently preferred embodiment the nickel on calcium phosphate catalyst used for steam reforming of hydrocarbons in accordance with this invention is promoted with barium.

Steam reforming of hydrocarbons, according to the invention, results in the formation of a gaseous product rich in methane.

The hydrocarbon feedstocks processable to methane-rich products according to the invention comprise hydrocarbons having from 2 to 15 carbon atoms per molecule. Such feedstocks preferably contain predominately paraffinic hydrocarbons such as propane, butane, hexane, cyclohexane, octane, cyclooctane, decane, dodecane, pentadecane and the like.

The carbon dioxide produced in either of the above processes can be removed by conventional methods, such as by absorption in an amine solution.

The following examples illustrate the invention:

EXAMPLE I

Five catalysts having the general configuration as nickel promoted calcium phosphate materials were prepared in different manners and subsequently employed for the steam reforming of cyclohexane. Catalyst A was prepared according to the method of this invention. The remaining catalysts are control catalysts. Catalyst B was prepared by a prior art method. Catalysts C, D and E were prepared by coprecipitating the nickel with the calcium phosphate.

Catalyst A was prepared by adding an aqueous solution of dipotassium hydrogen phosphate (1.0 mole) with vigorous stirring to an aqueous solution of calcium acetate (1.67 moles) to obtain a calcium phosphate gel having a Ca/P atomic ratio of 1.67. After standing overnight, the gel was recovered by filtration and washed by slurrying in a 3500 ml portion of water and filtered. The wash treatment was done three times. Finally, the filter cake was additionally washed by pulling 10 liters of distilled water through it. About ¼ of the wet cake was reslurried in 1000 ml of distilled water and to the stirred slurry was added 16 g of barium nitrate dissolved in 300 ml of distilled water. The mixture was allowed to stand for 2 days with occasional stirring. Then to the well-stirred slurry was slowly added a mixture of 145 g nickel nitrate and 16 g barium nitrate dissolved in 600 ml of hot distilled water and 100 g potassium carbonate dissolved in 250 ml of distilled water. The resulting mixture was filtered to obtain a cake which was reslurried in about 3500 ml of distilled water and filtered. This operation was repeated and finally about 3 liters of distilled water was pulled through the filter cake. The cake was dried overnight at 220° F, crushed to pass a 40 mesh screen and calcined in air at 800° F for 3 hours. The cooled product was mixed with 3 weight percent polyethylene powder and pilled to ⅛-inch size at 100 psig. The pills were heated at about 800° F in hydrogen for about 20 minutes to obtain the finished catalyst. This invention catalyst, as analyzed, contained 16.3 weight percent barium and 26.9 weight percent nickel based on the total weight of the catalyst composite. The surface area of the catalyst was about 80 square meters per gram, as determined by nitrogen absorption, the pore volume was about 0.2 ml per gram as determined by water absorption, and the apparent bulk density was 0.94 gram per ml.

Catalyst B is a control catalyst made in the manner described in U.S. Pat. No. 3,149,081 by adding a solution obtained by dissolving 110 g nickel carbonate to a total of 324 g of 85 percent $H_3PO_4$ contained in 736 ml of hot water. The clear dark green solution was added with vigorous stirring to a slurry of 352 g of calcium hydroxide in water. The atomic ratio of Ca to P was about 1.67 to correspond to the formation of calcium hydroxyapatite. After standing overnight, the gel was filtered and dried overnight at 220° F. The product was crushed to pass a 40 mesh screen and resulting material was calcined at 800° F in air for 2 hours. The cooled product was mixed with 4 weight percent polyethylene powder, pilled and reduced in hydrogen as described for catalyst A. Analysis showed the catalyst to contain 8.9 weight percent nickel. The surface area was about 61 square meters per gram and the pore volume was about 0.6 ml gram.

Catalysts C, D and E are control catalysts made by modifying the method used in preparing catalyst B to incorporate more nickel and to add barium as a promoter. In these preparations, a solution containing nickel nitrate and orthophosphoric acid was added to a slurry of calcium hydroxide in water. In each instance, a 1:2:3.68 mole ratio of $H_3PO_4$ to $Ni(NO_3)_2$ to $Ca(OH)_2$ was used. The manner of adding the barium promoter was somewhat different in each preparation, however. For catalyst C, a 4:1 nickel to barium atomic ratio was used, half the barium being added as barium nitrate to the nickel nitrate-phosphoric acid solution and the other half impregnated as barium acetate solution onto the dried and calcined product. For catalyst D, a 4:1 nickel to barium atomic ratio was used but the entire amount of barium was added to the nickel nitrate-phosphoric acid solution prior to adding the total solution to the calcium hydroxide. For catalyst E, a 5:1 nickel to barium atomic ratio was employed and the barium as a solution of barium acetate was added to the mixture resulting from the addition of the nickel nitrate-phosphoric acid solution to the calcium hydroxide slurry. Catalyst C was dried, crushed, sieved and calcined in air at 800° F in the form of 10–20 mesh material. This catalyst was not pilled. Catalyst D was dried and calcined in a similar manner but 10–40 mesh material was retained as the final catalyst. This catalyst was not pilled. Catalyst E was treated similarly to catalyst D except it was used in the form of material passing a 60 mesh screen. Catalyst C was analyzed and found to be composed of 10.3 weight percent barium, 26.8 weight percent nickel, 15.8 weight percent calcium and 7.1 weight percent phosphorus. The surface area of the catalyst was about 51 square meters per gram and it had a pore volume of about 0.3 ml per gram. Catalyst D was analyzed and found to be composed of 1.03 weight percent barium, 34.5 weight percent nickel, 15.8 weight percent calcium and 9.3 weight percent phosphorus. The surface area of the catalyst was about 114 square meters per gram and the pore volume was about 0.6 ml per gram. Catalyst E was analyzed and found to be composed of 2.52 weight percent barium, 27.8 weight percent nickel, 18.8 weight percent calcium and 7.5 weight percent phosphorus. The surface area of the catalyst was about 74 square meters per gram and the pore volume was about 0.5 ml per gram.

EXAMPLE II

The catalysts of Example I were tested for steam reforming cyclohexane in a fixed bed reactor at about 850° F and a pressure of 300 psig (about 2.067 MPa). The cyclohexane was supplied to the reactor at a weight hourly space velocity (WHSV) of 2. The steam to hydrocarbon weight ratio was about 1.6:1.

Each catalyst was charged to a reactor and reduced with hydrogen for about 30 minutes while bringing the reactor up to reforming temperature.

The following data were obtained:

Table I

| Run | Catalyst | Ni, wt. % | Ba, wt. % | Useful Life |
|---|---|---|---|---|
| 1 | A | 26.9 | 16.3 | 2550 |
| 2 | B | 8.9 | None | <40 |
| 3 | C | 26.8 | 10.3 | 150 |
| 4 | D | 34.5 | 1.0 | 800 |
| 5 | E | 27.8 | 2.5 | 1050 |

In the above table, the term "Useful Life" is an expression of the weight of cyclohexane converted per unit weight of catalyst. Each of the above runs was terminated when the conversion of feedstock dropped below about 99 percent. During the first 90 percent of Run 1, conversion of cyclohexane was in excess of 99.5 percent with a typical gas analysis of 8.5 volume percent hydrogen, 0.5 volume percent CO, 24 volume percent carbon dioxide and 67 volume percent methane. On the last day of the run, the conversion was 98.2 percent with the gas analysis showing 11.2 volume percent hydrogen, 0.5 volume percent CO, 24 volume percent carbon dioxide and 64.3 volume percent methane.

EXAMPLE III

Catalyst F was prepared according to the method of this invention by mixing together aqueous solutions of calcium nitrate (0.375 mole) and dipotassium hydrogen phosphate (0.25 mole) to make a gel in which the atomic ratio of Ca to P was 1.5:1. To the gel was added 1 mole of potassium hydroxide in 300 ml of water followed by the slow addition of 0.5 mole nickel nitrate dissolved in 400 ml of water. An additional 0.36 mole of KOH dissolved in 300 ml of water was then added to the creamy precipitate with continued stirring for 30 minutes more. The nickel hydroxide-calcium phosphate gel was filtered, washed twice by reslurrying in water and filtering and the cake was dried at 220° F. The dry cake was sieved through 40 mesh giving 99 g of dry material. Ninety-five grams of this material was impregnated with an aqueous solution containing 9.3 grams of barium acetate and the resulting paste was redried at 220° F for 16 hours. The dry powder was pilled to ⅛-inch tablets using 3 weight percent graphite as a die lubricant. The pills were reduced in hydrogen at 700° F for 2 hours. The final catalyst was analyzed and found to be composed of 6.9 weight percent barium, 33.2 weight percent nickel, 15.3 weight percent calcium and 9.3 weight percent phosphorus. The surface area of the catalyst was about 123 square meters per gram.

The pilled catalyst was tested for steam reforming of cyclohexane in the reactor previously used. A 1.1 WHSV hydrocarbon feed rate was used at a temperature of 800°–880° F, pressure of 300 psig and a weight ratio of steam to hydrocarbon of 2:1. Complete conversion of the cyclohexane was achieved over the 350 hour test period. Typical effluent compositions at the end of 17 hours and 324 hours are shown.

Table II

| Component, Mole % | 17 hours | 324 hours |
| --- | --- | --- |
| Hydrogen | 9.86 | 10.63 |
| Carbon monoxide | 0.03 | 0.14 |
| Carbon dioxide | 23.26 | 23.15 |
| Methane | 66.85 | 66.08 |

Consideration of the test results shows that catalysts prepared in the manner of the invention are effective in steam reforming of hydrocarbons.

EXAMPLE IV

Catalyst G was prepared according to the method of this invention by forming a calcium phosphate gel by mixing together with vigorous stirring aqueous solutions containing 167 g calcium acetate in one solution and 87 g dipotassium hydrogen phosphate in the other. The atomic ratio of calcium to P was 1.67:1. The gel was filtered, reslurried three times in water, filtering each time, and given a final wash by pulling about 1.5 liters of water through the filter cake. The cake was then reslurried in water and to it was added an aqueous solution containing 62 g $UO_2(NO_3)_2 \cdot 6H_2O$ dissolved in water and the mixture was allowed to stand overnight. The mixture was then filtered (all the yellow color was now in the precipitate). The filter cake was reslurried in water and to the slurry while maintaining vigorous stirring was slowly and simultaneously added an aqueous solution containing 290 g of $Ni(NO_3)_2 \cdot 6H_2O$ and 62 g of $UO_2(NO_3)_2 \cdot 6H_2O$, and an aqueous solution containing 150 g of KOH. The resulting mixture was filtered to obtain a filter cake which was reslurried three times in water, filtering each time, and the cake was given a final wash by pulling 2 liters of water through it. The wet cake was dried at 220° F. The dried cake was crushed and sieved. The final catalyst was calculated to contain 26.8 weight percent uranium, 26.6 weight percent nickel, 14.9 weight percent calcium and 6.9 weight percent phosphorus, based on theoretical considerations.

The catalyst in the form of 60–200 mesh particles was charged to a fluidized bed reactor and the reactor was heated to 600° F (315° C) and pressured to 150 psig with hydrogen to reduce the catalyst. The heating time in this step was 30 minutes. The hydrogen flow was discontinued and a mixture of carbon monoxide and water was introduced as feed. During the run, pressure was varied from 150 to 300 psig, temperature ranged from 550° to 800° F, the mole ratio of water to carbon monoxide was about 3:1 and a gaseous hourly space velocity of carbon monoxide ranging from about 1200 to 2000 was employed. Almost complete conversion of carbon monoxide was obtained, i.e., effluent analysis showed a carbon monoxide content ranging from about 0.04 mole percent or less. The product ratios on a dry basis varied somewhat with pressure and temperature but generally fell in the ranges:

| Hydrogen | 2 – 18 mole percent |
| --- | --- |
| Carbon dioxide | 65 – 75 mole percent |
| Carbon monoxide | 0.01 – .04 mole percent |
| Methane | 15 – 25 mole percent |

The product gas can be treated conventionally to remove carbon dioxide (by absorption in amine solutions) to obtain a final product which would be fungible with natural gas.

It will be evident to those skilled in the art that various modifications of this invention can be made, or followed, in the light of the foregoing disclosure and discussion, without departing from the spirit or scope thereof.

What is claimed is:

1. A catalyst composition consisting essentially of nickel, a metal selected from the group consisting of barium and uranium, combined oxygen and a calcium phosphate support having a Ca:P atomic ratio in the range of 1.4:1 to 2.3:1, wherein the compounds are present in approximate amounts, as follows:

| Calcium | 5 to 35, |
| --- | --- |
| Phosphorus | 2 to 20, |
| Nickel | 10 to 50, and either |
| Barium | 1 to 20, or |
| Uranium | 2 to 40, | all said amounts expressed in terms of weight percent, based upon the weight of the total catalyst.

2. The composition of claim 1 wherein the components are present in approximate amounts, as follows:

| Calcium | 10 to 25, |
| --- | --- |
| Phosphorus | 5 to 15, |
| Nickel | 20 to 40, and either |
| Barium | 2.5 to 18, or |
| Uranium | 10 to 30, | all said amounts expressed in terms of weight percent, based upon the weight of the total catalyst.

3. The composition of claim 1 wherein said Ca:P ratio is about 1.67:1.

4. A composition in accordance with claim 3 containing about 26.9 weight percent nickel and about 16.3 weight percent barium, based upon the weight of the total catalyst.

5. The composition of claim 1 wherein said Ca:P ratio is about 1.5:1.

6. A composition in accordance with claim 5 containing about 33.2 weight percent nickel and about 6.9 weight percent barium, based on the weight of the total catalyst.

7. A composition in accordance with claim 3 containing about 26.6 weight percent nickel and about 26.8 weight percent uranium, based on the weight of the total catalyst.

8. A method for preparing a catalyst composition consisting essentially of nickel, a promoter selected from the group consisting of barium and uranium, combined oxygen and a calcium phosphate support having a Ca:P atomic ratio in the range of 1.4:1 to 2.3:1 which comprises admixing an aqueous solution of a soluble calcium salt and an aqueous solution of a soluble phosphate salt to form a calcium phosphate gel having a Ca:P atomic ratio in the range of 1.4:1 to 2.3:1, introducing into said gel an aqueous solution of nickel and an aqueous solution of barium or uranium, recovering the promoted gel, drying said promoted gel and thereafter heating the catalyst composition at a temperature in the approximate range of 300°–650° C.

9. The method of claim 8 wherein the components are present in the final catalyst composition in approximate amounts as follows:

| | |
|---|---|
| Calcium | 5–35, |
| Phosphorus | 2–20, |
| Nickel | 10–50, and either |
| Barium | 1–20, or |
| Uranium | 2–40, | wherein all said amounts are expressed in terms of weight percent, based upon the weight of total catalyst.

10. The method of claim 8 wherein a first portion of said promoter is introduced to said gel, the resulting mixture is allowed to stand for a period in the range of about 4 hours to about 4 days, to the thus partially promoted gel is introduced the remaining portion of said promoter and said nickel compound, and wherein said catalyst composition is thereafter recovered.

11. The method of claim 8 wherein said nickel solution and said promoter solution are simultaneously introduced to said gel.

* * * * *